United States Patent [19]

Trissel et al.

[11] Patent Number: 5,723,865
[45] Date of Patent: Mar. 3, 1998

[54] X-RAY IMAGING DEVICE

[75] Inventors: Richard Trissel, Cardiff; Stephen Horton, Oceanside; Brett Spivey, Encinita; Lee Morsell, Del Mar, all of Calif.

[73] Assignee: ThermoTrex Corporation, San Diego, Calif.

[21] Appl. No.: 538,791

[22] Filed: Oct. 3, 1995

Related U.S. Application Data

[63] Continuation-in-part of Ser. No. 344,141, Nov. 23, 1994.

[51] Int. Cl.$^6$ .................................................. G01T 1/202
[52] U.S. Cl. ..................... 250/368; 250/370.11; 378/37
[58] Field of Search ........................... 250/368, 370.11, 250/487.1; 378/191, 37

[56] References Cited

U.S. PATENT DOCUMENTS

| | | | |
|---|---|---|---|
| 3,790,785 | 2/1974 | Paolini et al. | 250/368 |
| 3,944,835 | 3/1976 | Vosburgh | 250/368 |
| 4,210,812 | 7/1980 | Ando et al. | 378/191 |
| 4,560,882 | 12/1985 | Barbaric et al. | |
| 4,631,409 | 12/1986 | Sparacia et al. | 250/368 |
| 4,987,307 | 1/1991 | Rizzo et al. | 250/370.11 |

*Primary Examiner*—Carolyn E. Fields
*Attorney, Agent, or Firm*—Fish & Richardson P.C.

[57] ABSTRACT

An x-ray imaging device. One surface of a flat single crystal CsI crystal is supported on an optically transparent support plate. The opposite surface, i.e. an x-ray illumination surface of the crystal is coated with an x-ray transparent optical reflector to provide an x-ray scintillation sandwich having an optical mirror at the x-ray illumination surface of the CsI crystal. An optical camera is preferably focused on the illumination surface of the CsI crystal. In a preferred embodiment an index of refraction matched optical adhesive is used at the x-ray illumination surface to attach the reflector and to reduce Fresnel reflections.

17 Claims, 8 Drawing Sheets

X-RAY IMAGING DEVICE

This is a continuation-in-part application of Ser. No. 08/344,141 filed Nov. 23, 1994. The present invention relates to x-ray imaging devices and specifically to digital x-ray devices.

BACKGROUND OF THE INVENTION

Most x-ray imaging devices involve directing a beam of x-rays through an object onto a phosphor screen which converts each x-ray photon into a large number of visible photons. The visible photons expose a sheet of photographic film placed close to the phosphor thus forming an image of the attenuation of x-rays passing through the object.

There are several limitations to film-screen x-ray devices. A major limitation is that the film serves the combined purpose of both the image acquisition function and the image display function. In addition, the range of contrast or latitude of the film is too limited to display the entire range of contrast in many objects of interest. Because of the limited latitude and dual acquisition/display function of film, a film-screen x-ray is often overexposed in one area and underexposed in another area due to the thickness and composition variations of the object across the image. The gray-scale level of x-ray film has a sigmoidal response as a function of exposure which results in difficulties in distinguishing contrast differences at the extremes of the exposure range; that is, in the most radiodense and in the most radiolucent areas of the image.

Digital x-ray techniques have been proposed as a technology which replaces the phosphor/film detector with a digital image detector, with the prospect of overcoming some of the limitations of film-screens in order to provide higher quality images. A potential advantage of digital x-ray technology involves the separation of the image acquisition function from the image display function. Digital detectors also provide a much greater range of contrast than film and the contrast response function is linear over the entire range. This would allow a digital detector to more easily distinguish subtle differences in attenuation of x-rays as they pass through various paths of the object. Differences in attenuation due to thickness and composition variations across the object can be subtracted out of the digital data in the computer and the residual contrast can then be optimized for the particular viewing mechanism, be it film or computer monitor. The residual contrast differences can then be analyzed to search for things of interest. Other advantages of digital x-ray technology include digital image archival and image transmission to remote locations for viewing purposes.

Two recent patents disclose systems which digitally image a small area of the breast in order to facilitate needle placement for needle-core biopsy. In the system manufactured by LORAD Medical Systems and described in U.S. Pat. No. 5,289,320 (issued Feb. 22, 1994 to Pellegrino, et al.), a light emitted phosphor screen is coupled to a CCD array with a commercially available lens system. In a system manufactured by Fisher Imaging Corporation and described in U.S. Pat. No. 5,078,142 (issued Jan. 7, 1992 Siczek, et al.), light emitted from a phosphor screen is coupled to a CCD array with a fiber-optic taper.

Current digital x-ray devices have fairly limited resolution and so they are limited in their applications. What is needed is a better digital x-ray device.

SUMMARY OF THE INVENTION

The present invention provides an x-ray imaging device. One surface of a flat single crystal CsI crystal is supported on an optically transparent support plate. The opposite surface, an x-ray illumination surface, of the crystal is coated with an x-ray transparent optically reflecting material to provide an x-ray scintillation sandwich having an optical mirror at the x-ray illumination surface of the CsI crystal. An optical camera is focused on the illumination surface of the CsI crystal. In a preferred embodiment an optical grade adhesive is used at the x-ray illumination surface to attach the reflector and to reduce Fresnel reflections.

DETAILED DESCRIPTION OF PREFERRED EMBODIMENT

Preferred embodiments of the present invention are described below by reference to the figures.

First Preferred Embodiment

Figure 1:
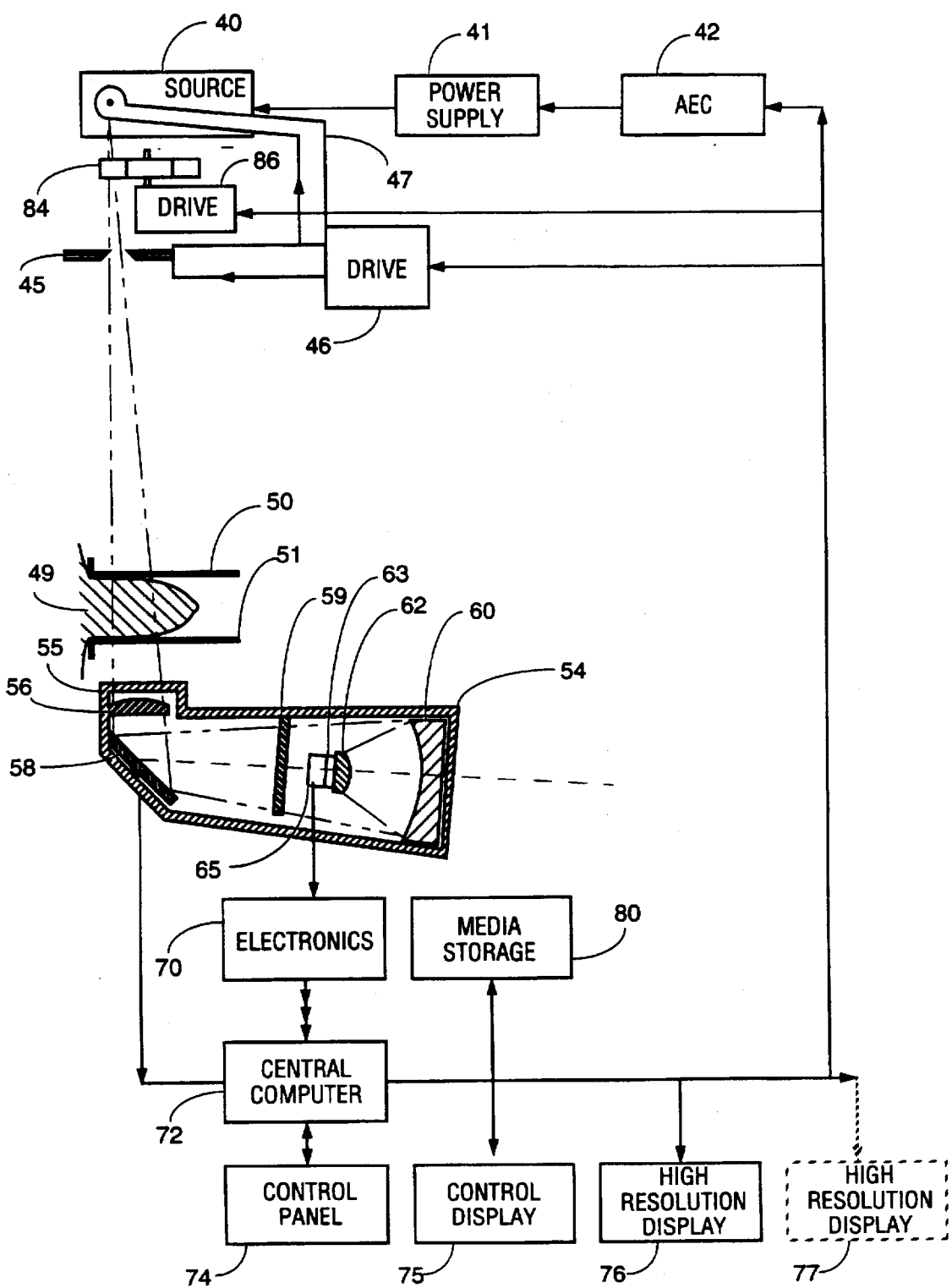
FIG. 1 is a schematic drawing showing the principal elements of a first preferred embodiment of the invention fabricated by inventors and their co-workers.

A schematic of the key elements of a first preferred embodiment of a digital mammography device is shown in FIG. 1. The device consists of an x-ray source 40, a conventional breast compression mechanism 50, and a digital detector system 54.

The preferred embodiment utilizes an x-ray source 40 which incorporates a standard Model B110/M149 VariardEimac x-ray generation tube with tungsten anode. High voltage power is applied to the x-ray source 40 with power supply 41. An x-ray filter wheel 84 has different x-ray filters, fabricated from aluminum, silver, iodine and rhodium, for example. A specific filter in the filter wheel 84 is automatically selected by filter wheel drive 86 which is linked to the central computer 72. This embodiment locates the x-ray tube 3 at 0 elevation (relative position), aperture 45 at 15 cm, the breast tray 50, 51 at 60 cm, and the front surface of the scintillator 55 at 63 cm.

Figure 2:
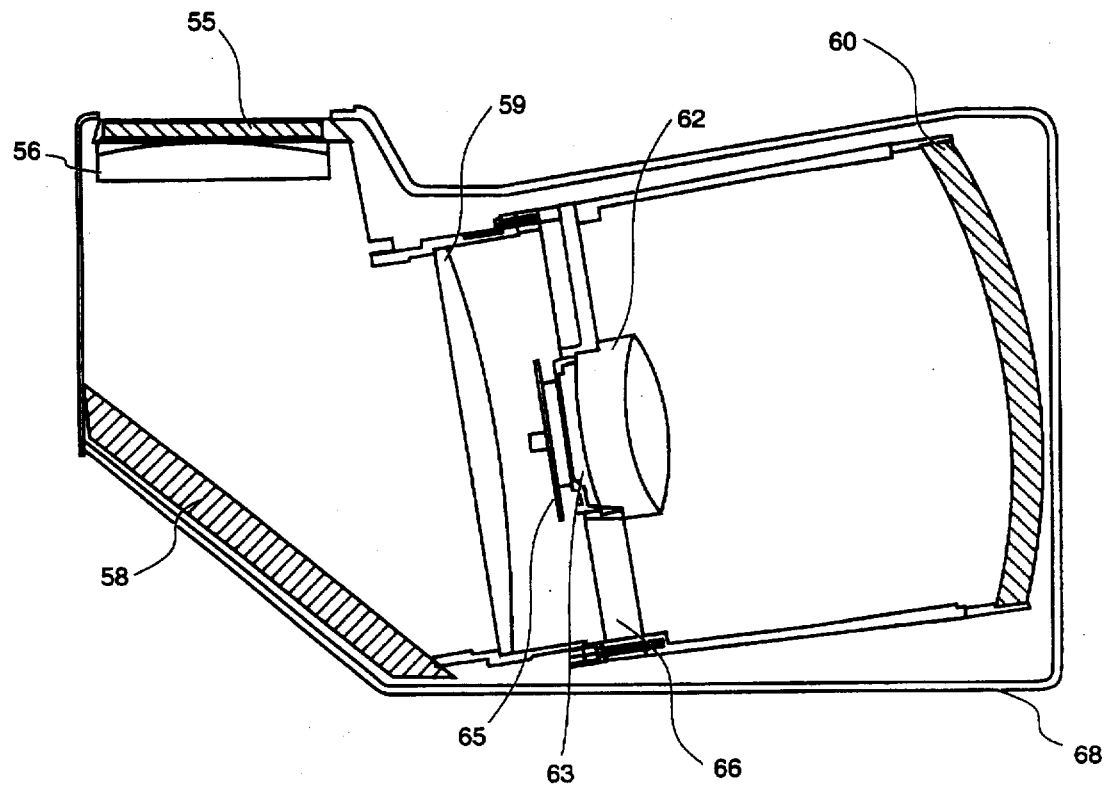
FIG. 2 is a drawing showing the principal parts of the x-ray detector assembly in the first preferred embodiment of the invention.

The digital detector assembly 54 displayed in FIG. 2 consists of a scintillator assembly 55, and a f10.83 Schmidt optical system consisting of a field lens 56, flat mirror 58, aspherical Schmidt corrector plate 59, and spherical primary mirror 60 which focuses the light into a doublet lens 62, finally forming an image on a CCD array 63. The entire digital detector assembly 54 is enclosed in a sealed housing 68 to eliminate dust and ambient visible light.

Figure 3A:
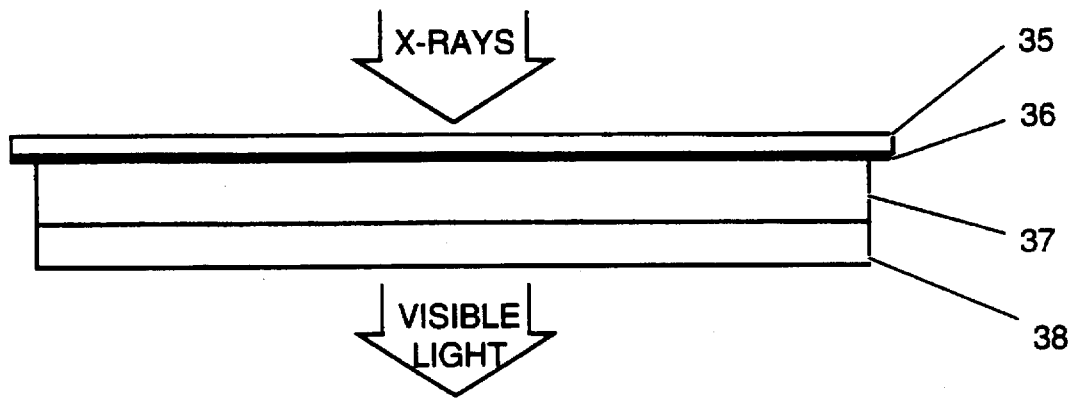
FIG. 3A, 3B and 3C show three methods of fabricating an efficient x-ray to a visible light converter.
Figure 3B:
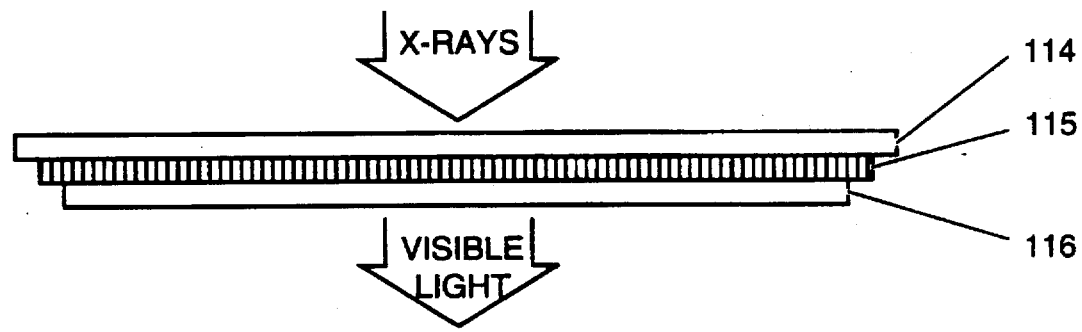
Figure 3C:
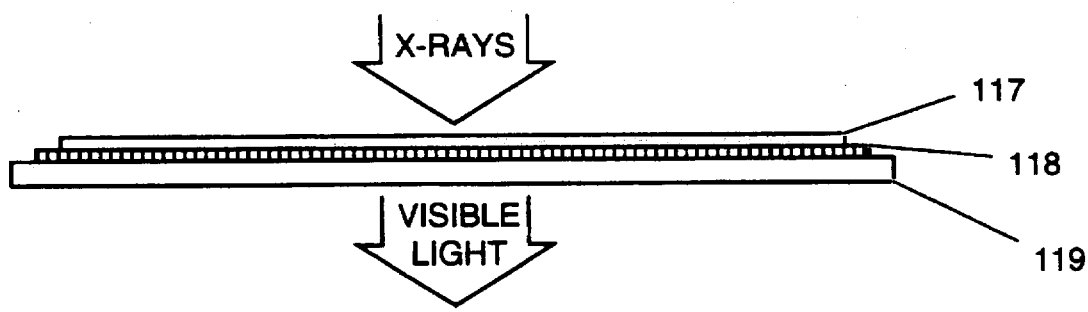

FIG. 3A, 3B and 3C discloses three methods for fabricating the scintillator assembly 55. Each x-ray photon striking the scintillator assembly 55 is converted into a large number of visible photons. The preferred embodiment allows a high percentage of x-rays to be absorbed by the scintillator, a corresponding high number of visible photons to be converted for each x-ray photon, and a high percentage of visible photons to exit the rear surface of the scintillator.

FIG. 3A displays a preferred method of fabricating the scintillator assembly 55. We use a 7 cm×7 cm×0.25 cm thick optically transparent scintillator crystal 37. The preferred scintillator material 37 is a thallium-doped cesium iodide CsI (T1) crystal which is "optically surfaced" on both sides of the thickness dimension. Another possible scintillator crystal is thallium-doped sodium iodide. The fragile CsI scintillator 37 is bonded to a 0.25 cm thick sheet of optically transparent polycarbonate 38 to provide structural rigidity. A separate 0.1 cm thick sheet of polycarbonate 35 is coated with a visible high reflectance coating 36 such as a thin aluminum, in order to provide reflectance for visible light. The reflector coated side of the polycarbonate sheet 35 is bonded to the top of the scintillator 37. The polycarbonate sheet 35 is then machined to a thickness of about 0.025 cm in order to minimize the attenuation of x-rays passing through the sheet 35. We calculate that for 17 to 30 keV x-ray photons such as those used for x-ray mammography imaging, for example, that greater than 98% of the x-rays striking the scintillator assembly 55 pass through the polycarbonate sheet 35 and the reflector coating 36 and are absorbed in the first 200 microns of the scintillator 37 which converts each x-ray photon into a large number of visible photons. These visible photons are emitted into 4 $\pi$steradians. Photons hitting the reflector coating 36 are reflected back towards the optical system, thus effectively doubling the visible light collected by the CCD array 63. A visible light image representing the attenuation of x-rays through the sample 49 is therefore produced at the front surface of the scintillator 37.

The first preferred embodiment utilizes a commercially available Model KAF-1000 CCD array 63 (Kodak Corporation) containing an array of 1024×1024 pixels. The size of each pixel is 24 microns×24 microns resulting in a 2.5 cm×2.5 cm imaging area. The Schmidt optical system provides a magnification ratio of 2.75 between the CCD array 63 and the front surface of the scintillator 37. The separation distance of about 3 cm between the breast 49 and the x-ray absorbing surface of the scintillator 37 produces a slight geometrical magnification of 1.05 of an object of the breast tray 50, 51. In addition, this separation distance contributes to the reduction of the background signal produced by x-rays scattered by the breast 49. This results in an equivalent pixel size of 66 microns×66 microns at the breast tray 50, 51. The imaging area is then 6.7 cm×6.7 cm at the scintillator assembly 55 and 6.5 cm×6.5 cm at the breast tray 50, 51. The spectral response characteristics of the CCD array 63 are selected to provide the most efficient detection of the visible photons emitted by the scintillator assembly 55.

A drive/preamplifier electronics assembly 65 is provided at the CCD 63, with cables leading to external detector electronics assembly 70 which contains analog-to-digital conversion circuitry to convert the analog CCD data into 12-bit digital values at a 5 MHz readout rate. This digital data is then stored in the central computer 72. The central computer 72, a commercially available 586AT, is equipped with a high resolution display monitor 76, a very high resolution display monitor 77 to view the final images, and a media storage device 80 to store the images. A separate control panel 74 used to control the x-ray source 40 is linked with the central computer 72.

FIG. 3B disclosed an alternate method for fabricating the scintillator assembly 55. This method involves coating a 7 cm×7 cm×0.25 mm thick sheet of beryllium or polycarbonate 114 with a thin layer of visible high reflectance coating to provide efficient collection of visible photons. A 200 micron thin layer of dendritic cesium iodide 116 is then coated onto the reflector coated 115 side of the beryllium sheet. This allows a minimum number of x-ray photons to be absorbed by the beryllium and a very high number of x-ray photons to be converted each to a large number of visible photons. The reflector coating 115 helps to direct a high percentage of these visible photons towards the rear of the scintillator assembly 55.

FIG. 3C discloses a third method for fabricating the scintillator assembly 55. This embodiment provides a 200 micron thick layer of dendritic cesium iodide 118 on a 7 cm×7 cm×0.1 cm thick sheet of optical glass 119. A thin layer of as aluminum is then coated onto the dendritic cesium iodide. This allows a high percentage of x-ray photons to be converted into visible light and allows these visible photons to pass through the optical glass towards the rear of the scintillator assembly 55 with very little attenuation.

Second Preferred Embodiment

Figure 4:
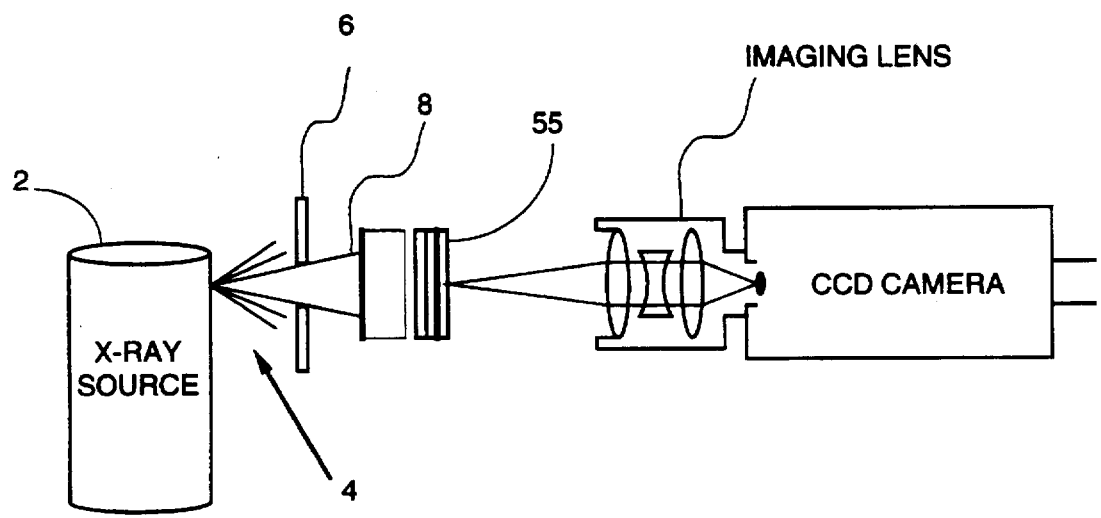
FIG. 4 is a sketch of a second embodiment of the present invention.

A second preferred embodiment of the present invention, which can be made very small and portable, is described by reference to FIG. 4 and FIGS. 3a,b, and c. A 40 kV, 10–60 watt x-ray source 2 (such as is supplied by Fine Focus Corporation) provides an x-ray beam 4 which is collimated by collimator 6 to produce collimated beam 8. An object 10 to be x-rayed is placed in the path of beam 8. A portion of the x-ray photons in beam 8 pass through object 10 and produce an x-ray shadow image on CsI (T1) scintillator 55. Scintillator 55 can be any of the three scintillators shown in FIGS. 3a, b or c. Scintillator 55 produces a visible light scintillator image corresponding to the x-ray shadow image. Lens system 12 in turn images the visible light scintillator image on to CCD detector array 14 of CCD camera 16.

The lens system we prefer for this embodiment is a NAVITAR f/0.95 25 mm CC TV lens and our choice of CCD cameras is a commercially available high-sensitivity, low noise miniature CCD camera such as those produced by Panasonic or Sony. A leaded glass window may be provided between scintillator 55 and CCP array 14 to protect x-ray sensitive electronic equipment.

Third Preferred Embodiment

Figure 5:
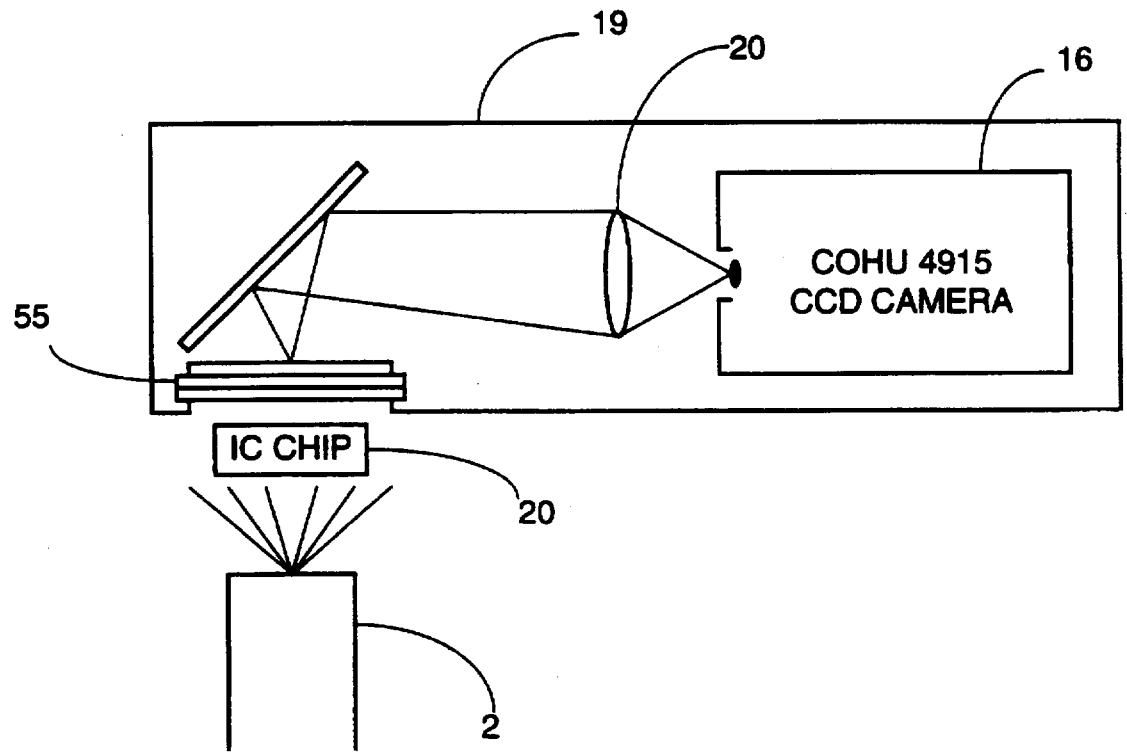
FIG. 5 is a sketch of a third embodiment of the present invention.

A third preferred embodiment of the present invention as shown in FIG. 5 is an x-ray camera for examining integrated circuit chips. As in the second preferred embodiment we use an x-ray source 2 described above. The chips being examined are positioned at 20 in FIG. 5.

In this application the scintillator 55 is either of the scintillators shown in FIG. 3A, 3B and 3C and described above. A flat fold mirror 15 directs light from the visible light scintillator image through lens system 12 (in this case a NAVITAR 25 mm f/0.95 CC TV lens) onto the CCD array of camera 16 (in this case a COHU 4915 CCD camera). Enclosure 19 is preferably a lead shielded light-tight aluminum enclosure. Fold mirror 15 permits camera 16 to be positioned out of the direct path of x-rays from source 2.

CsI Sandwich

FIGS. 6A through 6D display, in greater detail than that of FIG. 3A, 3B and 3C, our currently preferred method for fabricating the scintillator assembly 55. It is very important to produce scintillators having a very good optical quality reflecting surface. This is a problem because producing a very flat surface on CsI crystals is difficult. We use a 7 cm×7 cm 0.25 cm thick optically transparent single crystal scintillator 4. The preferred scintillator material is a thallium-doped cesium iodide CsI (T1) crystal which is surfaced on both sides to the thickness dimension desired (in this case about 0.25 cm) using a diamond fly cutting procedure or any other procedure which produces an optical quality surface with less than about 100 angstroms of surface roughness. We then bond an optical quality polycarbonate plate 5, which is about 0.40 cm thick, to the CsI crystal. We choose an optical grade adhesive 10 which is index-matched as well as possible to the CsI index of refraction. A preferred adhesive is Summers Labs UV74 mixed with 9-vinyl carbazole monomer which is cured with UV light. Its index of refraction when cured is 1.6. The polycarbonate plate 5 provides structural rigidity over the entire surface area of the crystal. The index of refraction of the polycarbonate plate (1.59) closely matches that of the CsI crystal and the adhesive closely matches both materials. Therefore, we minimize light scatter and other boundary interface artifacts in the final light image. Fresnel reflections at these interfaces cause losses through the sandwich as well as contribute to scattered light that can degrade image quality. A separate 0.1 cm thick sheet of polycarbonate 1 is coated with a thin layer of aluminum 2 to provide both very high reflectance of visible light within the crystal and stop any outside light from entering the crystal. The aluminum coated side of the polycarbonate sheet 1 is then bonded, using the same adhesive 10, to the top of the CsI crystal 4. Polycarbonate sheet 91 is then machined at the other side to a thickness of about 0.025 cm in order to minimize the attenuation of x-rays passing through the sheet 1. We calculate that for 17 to 30 keV x-ray photons such as are used for x-ray mammography imaging, for example, greater than 98% of the x-rays striking the scintillator assembly 55 pass through the polycarbonate sheet 91 and the aluminum coating 2 and are absorbed in the first 200 microns of the CsI crystal 4 which converts each x-ray photon into a large number of visible light photons. These visible photons are emitted into 4 $\pi$ steradians and the photons hitting the aluminum coating are reflected back towards the optical system thus effectively doubling the visible light collected by the CCD array shown in FIGS. 1, 2, 4, 5, or 7. A focused, visible light image representing the attenuation of x-rays through the object being x-rayed is therefore produced at the surface between the scintillator and the aluminum coating.

Essential to the usefulness of any general purpose scintillator is adequate structural integrity as well as resistance to any potentially damaging moisture while exposed to expected environmental conditions. The CsI (T1) and other related crystals are typically hygroscopic and therefore require a barrier between their outer surfaces and nearly all environments. We accomplished this sealing through the implementation of optical-quality polycarbonate plastic plates. Polycarbonate was chosen because its Coefficient of Thermal Expansion (CTE) in addition to its optical indexes is relatively close to that of CsI.

Figure 6A:
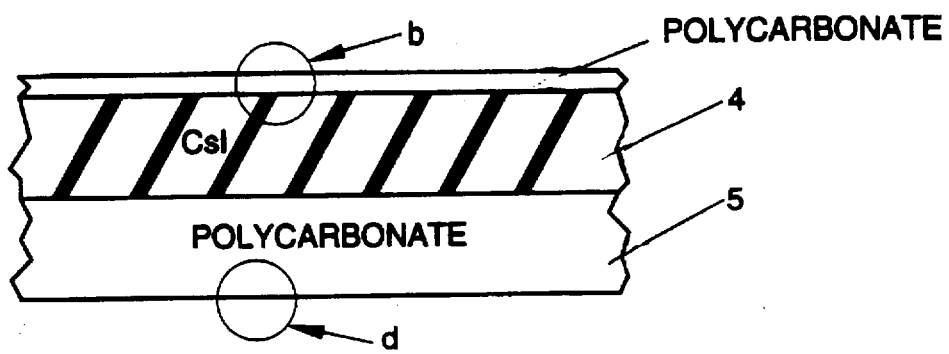
FIG. 6A through 6D shows the optical configuration of a preferred embodiment.
Figure 6B:
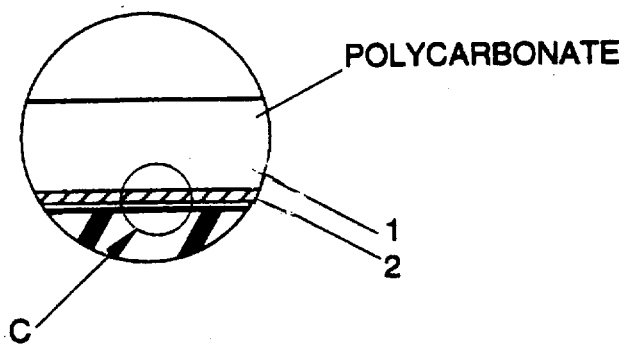
Figure 6C:
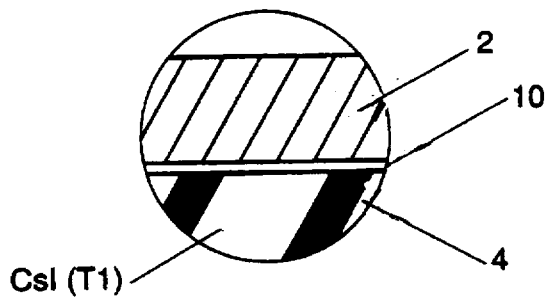
Figure 6D:
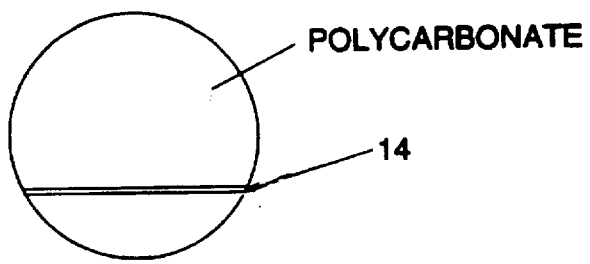
Figure 7:
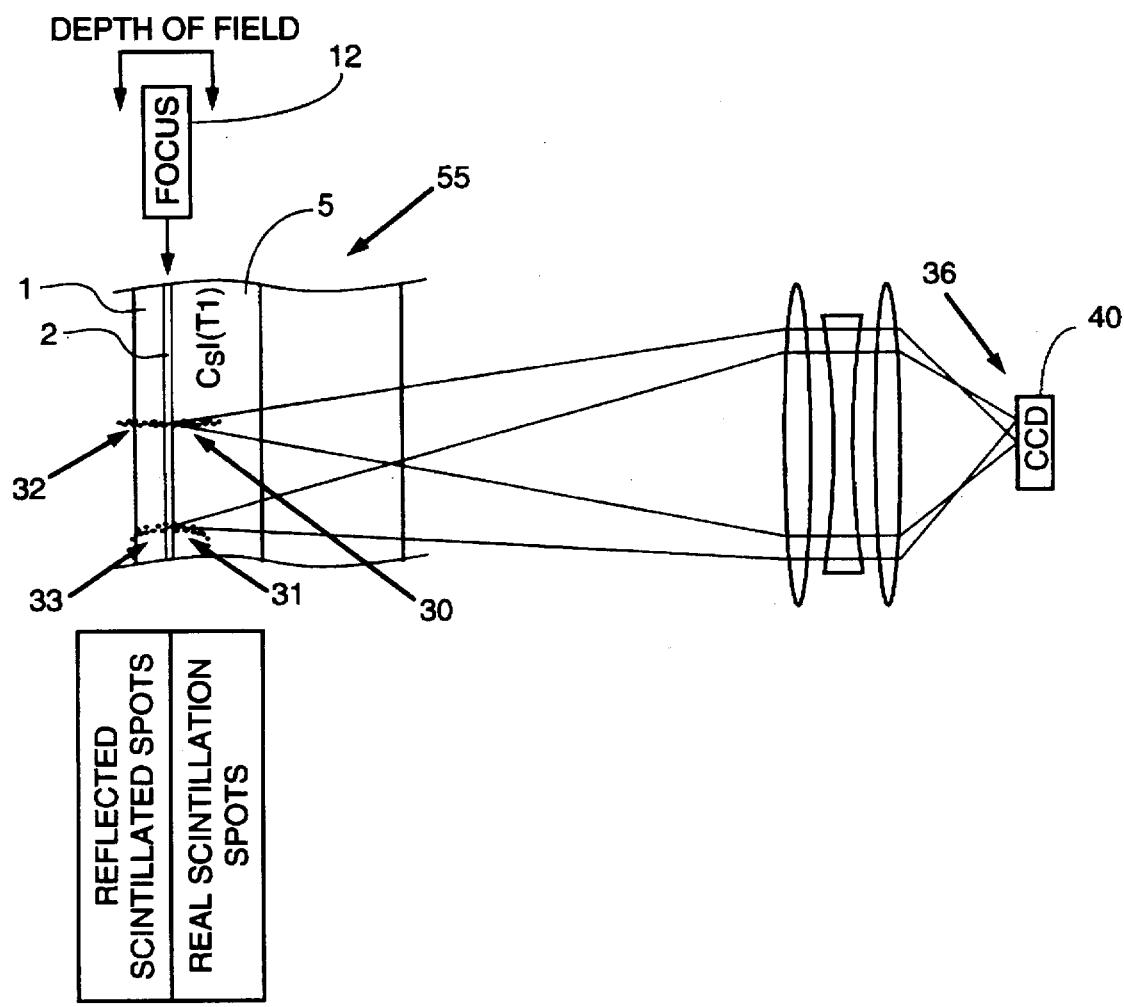
FIG. 7 shows how to focus the camera in a preferred embodiment.

The substantially polycarbonate plate 5 which is placed on the optical side of the sandwich is also designed to enhance the structural integrity as well as seal out the moisture. The plate is relatively thick (~4 mm) and is Anti-reflection coated with coating 14 to minimize Fresnel reflections from its outer surface as shown by FIG. 6D. As indicated by the following formula optical indices of adjoining materials should be closely matched to reduce unwanted reflections.

$$R = \frac{(n_1 - n_2)^2}{(n_1 + n_2)^2}$$

where $n_1$=index of material, $n_2$=index of material 2 and R is the Fresnel reflection.

For our CsI crystal, the index of refraction at the peak scintillation wavelength (of 550 nm) is 1.793. The index of refraction for our optical adhesive is 1.6. This gives a Fresnel reflection of about 0.4% at the x-ray illumination surface of the crystal. It is important that this reflection be kept low especially at this junction. The reflection here should preferably be kept less than about 0.5%. For some applications we have learned that the reflection problem can become acute if the Fresnel reflection exceeds about 1%.

The overall thickness of our preferred scintillator sandwich is slightly larger than 3.5 mm consisting of the following layers starting at the x-ray incident side:

| | |
|---|---|
| Polycarbonate Top Layer | 0.25 mm |
| Aluminizing Reflector Layer | 0.01 mm |
| Optical Adhesive | 0.05 mm |
| CsI Crystal | 1.50 mm |
| Optical Adhesive | 0.05 mm |
| Polycarbonate Bottom Layer | 4.00 mm |
| Anti-Reflectant Coating | 0.01 mm |

Our single-crystal scintillator provides substantial advantages over prior art Dendridic (needle-type) crystals. Better x-ray conversion is also possible due to the allowable thicker scintillator depth, before degrading resolution beyond a usable extent. Use of a single crystal (as opposed to needle-type crystal which must be very thin for good resolution) permits us to focus the optical portion of our camera system at the reflector—CsI interface 12 (in FIG. 6C). This provides an extremely good image with very high resolution.

Sandwich With Index Matching Fluid

Figure 8A:
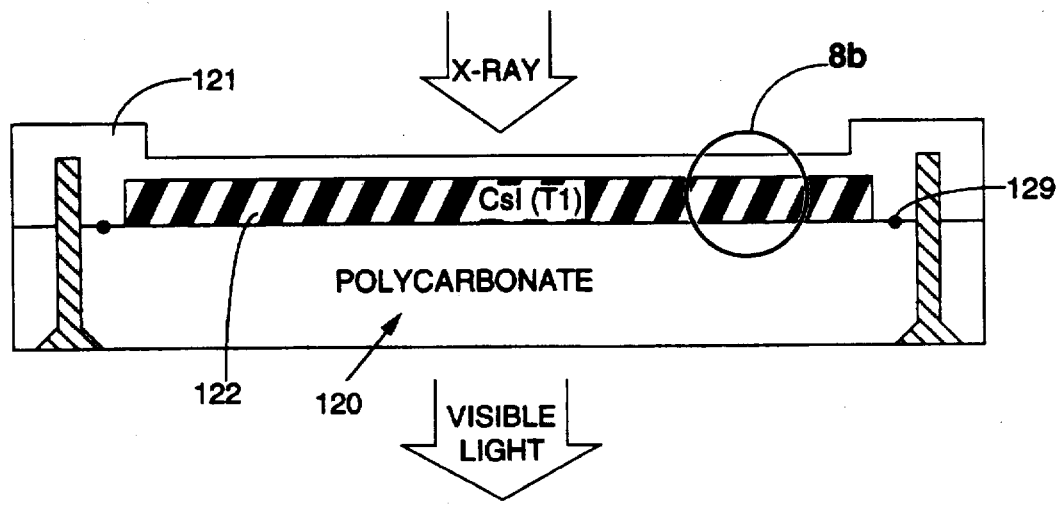
FIGS. 8A and 8B shows how to fabricate a preferred scintillator sandwich.
Figure 8B:
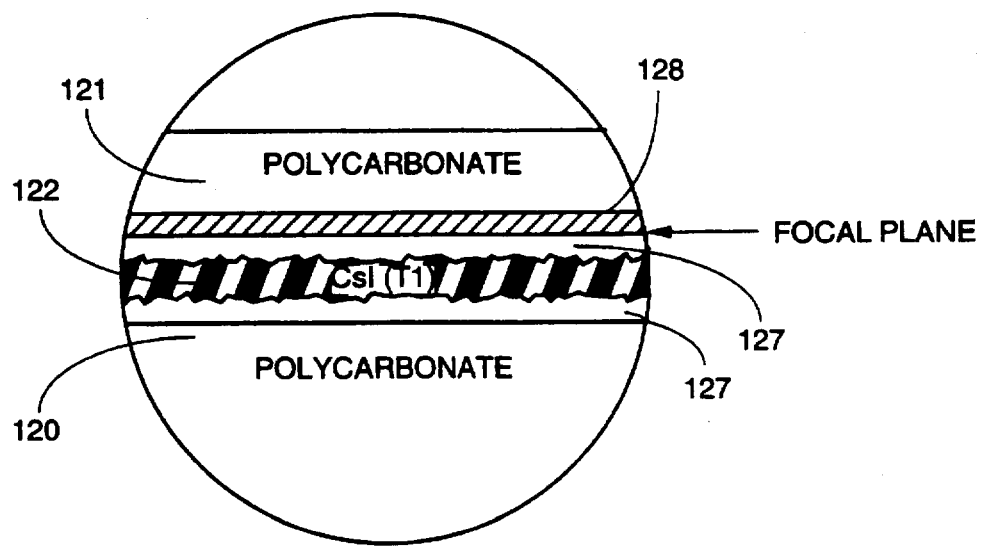

FIGS. 8A and 8B demonstrate another preferred scintillator sandwich incorporating the principals of the present invention. In this case the CsI crystal 122 is contained between polycarbonate base plate 120 and polycarbonate cover plate 121. Cover plate 121 as above is coated with a thin aluminum layer 128 to provide an x-ray transparent optically reflecting surface. The spaces between the crystal and the reflecting surface 128 of cover plate 121 is filled with an index matching fluid having an index refraction almost exactly matching that of the CsI crystal. We used in both spaces Cargille ηd=1.70, B-series index matching fluid. The thickness of the fluid was about 20 µm microns compared to a crystal thickness of about 1.5 mm. O-ring 129 assures a good seal. Note in FIG. 8B the thickness of spaces filled with the fluid is exaggerated. Note also we have emphasized the flatness of the mirror surface at the bottom of reflective layer 128 and the jaggedness of the upper and lower surfaces of CsI crystal 122 in order to indicate the importance of the index matching fluid in improving the optical performance of the sandwich. As indicated in FIG. 8B we focus our camera on the reflective surface which provides a very precise image of all scintillations in crystal 122 including the light reflected off the mirror. Because of the close match of the fluid and the crystal, there is virtually zero reflections from the rough surface of the CsI crystal.

Focusing the Optical System

Each x-ray photon typically generates one scintillator spot as it is absorbed in the CsI (T1) crystal. The greatest absorption location is at the point of x-ray entrance into the crystal, just down stream of aluminum mirror 2. However, many x-ray photons are absorbed at greater depths into the crystal. Spot locations within CsI crystal 5 are depicted at 30 and 31 in FIG. 7 as representing scintillations from about 20 absorptions. Each of these produce real images. Mirror 2 produces virtual images of these spots as represented at 32 and 33 in FIG. 7. Our optical system focal plane is at the mirror—CsI crystal interface as shown at 12 on FIG. 7 and we have provided an optical system with a depth of field that includes about 86% of the real and virtual scintillation spots. As shown at 36 in FIG. 7 large number of lined up spots (real and virtual in scintillator 55, which would be representative of narrow holes in the object being x-rayed) are imaged as points on CCD array 40.

While the above description contains many specifications, the reader should not construe these as limitations on the scope of the invention, but merely as exemplifications of preferred embodiments thereof. Those skilled in the art will envision many other possible variations are within it scope. CCD camera 16 could be any of many commercially available cameras which could produce either digital images or an analog image. An index matching fluid could be used as the interface between the illumination surface of the CsI crystal and the reflective surface of the reflector plate. For example, CARGILLE Company distributes an index matching fluid that closely matches the index of refraction of CsI the scintillator sandwich can be made as large as available crystal permits. Crystals as large as 24 inches by 24 inches are currently available. Good quality crystals as large as 12 inches by 12 inches are currently available. Accordingly, the reader is requested to determine the scope of the invention by the appended claims and their legal equivalents, and not by the examples which have been given.

We claim:

1. An x-ray scintillator for producing an x-ray image comprising:
   a) a substantially rigid optically transparent support plate; and
   b) a single crystal scintillation crystal in the form of a crystalline plate, defining a peak x-ray scintillation wavelength, mounted on said support plate, said scintillation crystal defining an x-ray illumination surface and a viewing surface, said illumination surface being covered with an x-ray transparent, optical reflector to define an optically reflecting illumination surface, and both viewing surface and said optically reflecting illumination surface being treated to reduce Fresnel reflections in said crystal at said peak x-ray scintillation wavelength to less than 1.0 percent and to reduce surface roughness to less than 100 angstroms;
   wherein said x-ray image is produced at and near said optically reflecting illumination surface directly from light created in said crystal and indirectly from light created in said crystal and reflected from said reflector.

2. A scintillator as in claim 1 wherein said scintillation crystal is a single crystal CsI crystal.

3. A scintillator as in claim 2 wherein said CsI crystal is doped to produce a CsI (T1) crystal.

4. A scintillator device as in claim 1 wherein said optical reflector is attached to said scintillation crystal with an optical grade adhesive.

5. A scintillator device as in claim 4 wherein said scintillation crystal defines a crystal index of refraction at said peak x-ray scintillation wavelength and said optical grade adhesive defines an adhesive index of refraction at said peak x-ray scintillation wavelength, said crystal index of refraction and said adhesive index of refraction being similar enough to reduce Fresnel reflections at said illumination surface to less than 0.5%.

6. A scintillator device as in claim 1 and further comprising an index matching fluid contained between said illumination surface and said optical reflector.

7. An x-ray device for producing x-ray images comprising:
   a) a substantially rigid optically transparent support plate; and
   b) a single crystal scintillation crystal in the form of a crystalline plate, defining a peak x-ray scintillation wavelength, mounted on said support plate, said scintillation crystal defining an x-ray illumination surface and a viewing surface, said illumination surface being covered with an x-ray transparent, optical reflector to define an optically reflecting illumination surface, and both viewing surface and said optically reflecting illumination surface being treated to reduce Fresnel reflections in said crystal at said peak x-ray scintillation wavelength to less than 1.0 percent and to reduce surface roughness to less than 100 angstroms;
   c) an optical camera defining a focal plane and a depth of field;
   wherein said camera and said scintillation crystal are positioned such that said depth of field includes said optically reflecting surface.

8. An x-ray device as in claim 7 wherein said scintillation crystal is a single crystal CsI crystal.

9. An x-ray device as in claim 8 wherein said CsI crystal is doped to produce a CsI (T1) crystal.

10. The x-ray imaging device as in claim 7 wherein said focal plane is centered on said reflecting surface.

11. An x-ray device as in claim 7 wherein said optical camera is a Schmidt camera.

12. An x-ray device as in claim 11 wherein said Schmidt camera comprises a spherical mirror, a Schmidt corrector plate, a CCD array, and an analog-to-digital conversion means for converting analog data from said CCD array to digital data.

13. An x-ray device as in claim 12 wherein said Schmidt camera also comprises a doublet lens located adjacent to said CCD array.

14. An x-ray device as in claim 11 wherein said Schmidt camera also comprises a lens located adjacent to said x-ray scintillation crystal.

15. An x-ray device as in claim 7 wherein said optical reflector is attached to said scintillation crystal with an optical grade adhesive.

16. An x-ray device as in claim 15 wherein said scintillation crystal defines a crystal index of refraction at said peak x-ray scintillation wavelength and said optical grade adhesive defines an adhesive index of refraction at said peak x-ray scintillation wavelength, said crystal index of refraction and said adhesive index of refraction being similar enough to reduce Fresnel reflections at said illumination surface to less than 0.5%.

17. An x-ray device as in claim 7 and further comprising an index matching fluid contained between said illumination surface and said optical reflector.

* * * * *